US008476484B2

(12) United States Patent
Demeneix et al.

(10) Patent No.: US 8,476,484 B2
(45) Date of Patent: Jul. 2, 2013

(54) TRANSGENIC CLAWED FROG EMBRYOS AND USE THEREOF AS DETECTORS OF ENDOCRINE DISRUPTERS IN THE ENVIRONMENT

(75) Inventors: Barbara Demeneix, Paris (FR); Nathalie Turque, Paris (FR)

(73) Assignees: Centre National de la Recherche Scientifique (CNRS), Paris (FR); The Museum National d'Histoire Naturelle, Paris (FR)

( * ) Notice: Subject to any disclaimer, the term of this patent is extended or adjusted under 35 U.S.C. 154(b) by 597 days.

(21) Appl. No.: 10/516,134

(22) PCT Filed: May 27, 2003

(86) PCT No.: PCT/FR03/01598
§ 371 (c)(1),
(2), (4) Date: Sep. 12, 2005

(87) PCT Pub. No.: WO03/102176
PCT Pub. Date: Dec. 11, 2003

(65) Prior Publication Data
US 2006/0101528 A1      May 11, 2006

(30) Foreign Application Priority Data

May 30, 2002 (FR) ..................... 02 06669

(51) Int. Cl.
*G01N 33/00* (2006.01)
*A01K 67/00* (2006.01)
*C12Q 1/00* (2006.01)

(52) U.S. Cl.
USPC ........................... 800/3; 800/8; 435/4

(58) Field of Classification Search
USPC .................. 800/3, 8, 20; 435/4, 325
See application file for complete search history.

(56) References Cited

U.S. PATENT DOCUMENTS

| 5,094,944 | A | 3/1992 | Hayes |
| 5,571,722 | A | 11/1996 | Rosson |
| 5,612,184 | A | 3/1997 | Rosson |
| 2006/0143718 | A1* | 6/2006 | Nebert ............................ 800/3 |

FOREIGN PATENT DOCUMENTS

| EP | 0859059 | * | 9/1998 |
| EP | 1 130 086 A | | 9/2001 |
| WO | WO-93/03179 A | | 2/1993 |
| WO | WO-98/28971 A | | 7/1998 |
| WO | WO-98/30715 A | | 7/1998 |
| WO | WO-01/88115 A | | 11/2001 |

OTHER PUBLICATIONS

Sheets, 1998, Nature Biotechnology, 16, 233-234.*
Kroll and Amaya, 1996, Development, 122, 3173-3183.*
West et al Genes and Development, 2002, 16: 271-288.*
Furlow et al Mol Endocrinol. 1999, 13(12):2076-89.*
Oofusa et al Environmental Toxicology and Pharmacology 13 (2003) 153-159.*
Oofusa et al Mol Cell Endocrinol. Jul. 5, 2001; 181(1-2):97-110.*
Chalfie et al Green fluorescent protein: properties, applications, and protocols, Wiley-Liss, New York, 1998 pp. 1-11, 246.*
Luez et al Proc Natl Acad Sci U S A. 1993, 1;90(15):7322-6.*
Pudney et al. 1973, Experiantia 29: 466-467.*
Turque et al Environ Health Perspect , 2005, 113:1588-1593.*
Ulisse et al Molecular and Cellular Endocrinology 126 (1997) 17-24.*
Turque et al., "A Rapid, Physiologic Protocol for Testing Transcriptional Effects of Thyroid-Disrupting Agents in Premetamorphic *Xenopus* Tadpoles," Environmental Health Perspectives, Nov. 2005, vol. 113, No. 11, pp. 1588-1593.
Arnheiter et al.; "Transgenic Mice with Intracellular Immunity to Influenza Virus"; (1990) Cell 62:51-61.
Argenton et al.; "An Activation Domain of the Helix-Loop-Helix Transcription Factor E2A Shows Cell Type Preference In Vivo in Microinjected Zebra Fish Embryos"; (1996) Mol Cel Biol 16:1714-1724.
Brinster et al.; "Regulation of metallothionein-thymidine kinase fusion plasmids injected into mouse eggs"; (1982) Nature 296:39-42.
Brown et al.; "*lac* Repressor Can Regulate Expression from a Hybrid SV40 Early Promoter Containing a *lac* Operator in Animal Cells"; (1987) Cell 49:603-612.
Brown et al.; "The thyroid hormone-induced tail resorption program during *Xenopus laevis* metamorphosis"; (1996) Proc. Natl. Acad. Sci. USA 93:1924-1929.
Capecchi et al.; "Altering the Genome by Homologous Recombination"; (1989) Science 244:1288-1291.
Ciana et al.; "Engineering of a Mouse for the in Vivo Profiling of Estrogen Receptor Activity"; (2001) Mol. Endocrinol 15:1104-13.
Coen et al.; *Xenopus* Bcl-$X_L$ selectively protects Rohon-Beard neurons from metamorphic degeneration; (2001) Proc. Natl. Acad. Sci. USA 98:7869-7874.
Day et al.; "Dual-Function Reporter Protein for Analysis of Gene Expression in Living Cells"; (1998) Biotechniques 25:848-850, 852-854, 856.
De Luze et al.; "Thyroid hormone-dependent transcriptional regulation of exogenous genes transferred into *Xenopus* tadpole muscle in vivo"; (1993) Proc. Natl. Acad. Sci. USA 90:7322-7326.
Denver et al.; "Basic Transcription Element-binding Protein (BTEB) Is a Thyroid Hormone-regulated Gene in the Developing Central Nervous System"; (1997) J. Biol. Chem 274(33):23128-34.
Deuschle et al.; "RNA Polymerase II Transcription Blocked by *Escherichia coli Lac* Repressor"; (1990) Science 2:480:483.
Hecht et al.; "A progesterone responsive element maps to the far upstream steroid dependent DNase hypersensitive site of chicken lysozyme chromatin"; Embo J. 7:2063-2073.

(Continued)

*Primary Examiner* — Anoop Singh
(74) *Attorney, Agent, or Firm* — Foley & Lardner LLP

(57) ABSTRACT

The invention relates to transgenic aquatic animals, particularly the clawed frog and the zebra fish and cells derived therefrom, characterized in comprising at least one expression cassette with a regulatory DNA sequence selected from the response elements to nuclear hormone receptors, particularly TRE, connected in a functional manner downstream of a DNA segment coding for a marker protein such as luciferase or GFP. The invention further relates to methods using the transgenic cells and animals according to the invention for the identification of endocrine disrupters in the environment.

5 Claims, 8 Drawing Sheets

OTHER PUBLICATIONS

Figure 1:
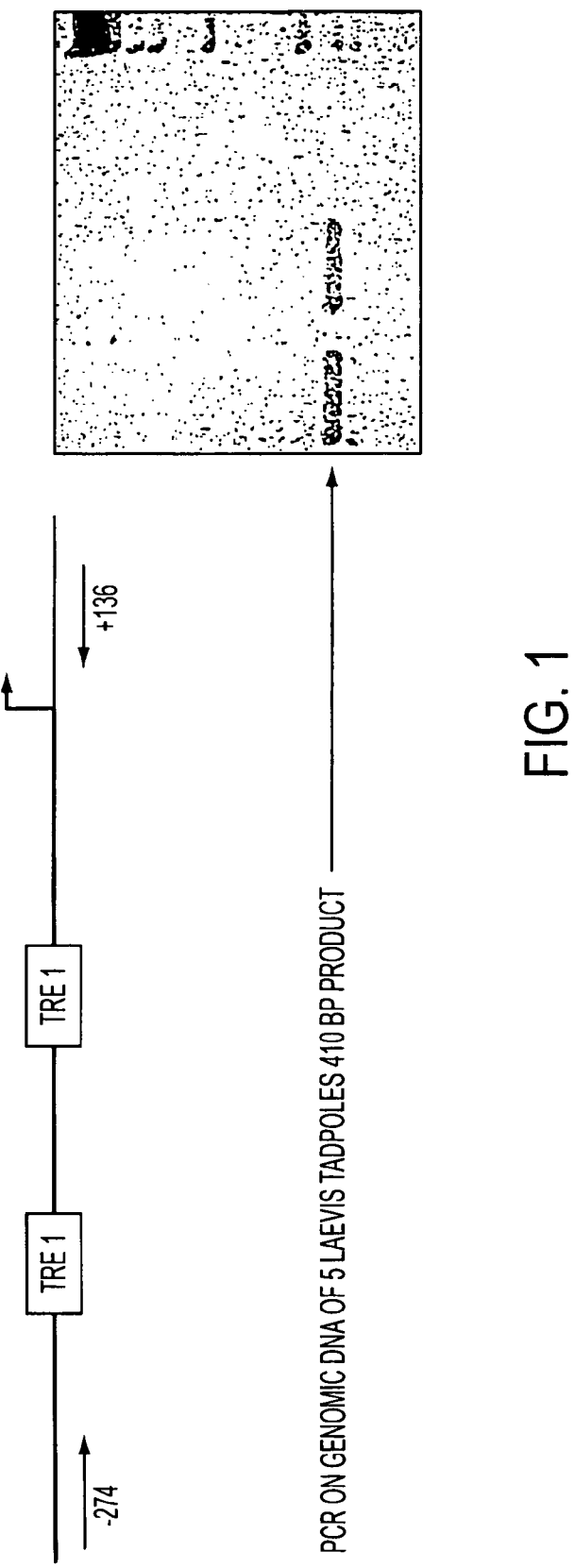

Hug et al.; "Organization of the Murine *Mx* Gene and Characterization of Its Interferon- and Virus-Inducible Promotor"; (1998) Mol. Cell. Biol. 8:3065.

Hynes et al.; "Hormone-responsive expression of an endogenous proviral gene of mouse mammary tumor virus after molecular cloning and gene transfer into cultured cells"; (1981) Proc. Natl. Acad. Sci. USA 78:2038-2042.

Ishizuya-Oka et al.; "Transient expression of stromelysin-3 mRNA in the amphibian small intestine during metamorphosis"; Cell and Tissue Res (1996) 283:325-329.

Karsenty; "Role of Cbfa1 in osteoblast differentiation and function"; (2000) Semin. Cell. Biol 11(5):343-6.

Kitazawa et al.; "Vitamin $D_3$ Augments Osteoclastogenesis via Vitamin D-Responsive Element of Mouse RANKL Gene Promoter"; (2002) Biochel Biophys Res Commun 290:650-655.

Klock et al.; "Oestrogen and glucocorticoid responsive elements are closely related but distinct"; (1987) Nature 329:734-736.

Kolla et al.; "Identification of a Mineralocorticoid/Glucocorticoid Response Element in the Human Na/K ATPase α1 Gene Promoter"; (1998) Biophys Res Commun.. 266:5-14.

Amaya and Kroll "A method for Generating Transgenic Frog Embryos"; (1999) Methods Mol Biol 97:393-414.

Labow et al.; "Conversion of the *lac* Repressor into an Allosterically Regulated Transcriptional Activator for Mammalian Cells"; (1990) Mol. Cell. Biol. 10:3343-3356.

Lee et al.; "Glucocorticoids regulate expression of dihydrofolate reductase cDNA in mouse mammary tumour virus chimaeric plasmids"; (1981) Nature 294:228-232.

Liu et al.; "Visualizing and quantifying protein secretion using a *Renilla* luciferase-GFP fusion protein"; (2000) Luminescence 15:45-9.

Luo et al.; "Molecular Cloning of a Novel Human Gene on Chromosome 4p11 by Immunoscreening of an Ovarian Carcinoma cDNA Library"; (2001) Biochem Biophys Res Commun.

Mader et al.; "Defining a minimal estrogen receptor DNA binding domain"; (1993) Nucleic Acids Res 21:1125-1132.

Mayo et al.; "The Mouse Metallothionein-I Gene is Transcriptionally Regulated by Cadmium following Transfection into Human or Mouse Cells"; (1982) Cell 29:99-108.

Metzger and Feil; "Engineering the mouse genome by site-specific recombination"; (1999), Curre. Opion. Biotechnol. 5:470-476.

Namciu et al.; "Human Matrix Attachment Regions Insulate Transgene Expression from Chromosomal Position Effects in *Drosophila melanogaster*" (1998) Mol. Cell. Biol 18:2382-91.

Ouatas et al.; "T3-dependent physiological regulation of transcription in the *Xenopus* tadpole brain studied by polyethylenimine based in vivo gene transfer"; (1998) Int. J. Dev. Biol. 42:1159-64.

Perez-Juste et al.; "An Element in the Region Responsible for Premature Termination of Transcription Mediates Repression of *c-myc* Gene Expression by Thryoid Hormone in Neuroblastoma Cells"; (2000) J. Biol. Chem 275:1307-14.

Shapiro et al.; "Differential Transcriptional Regulation of Rat Vasopressin Gene Expression by Estrogen Receptor α and β"; (2000) Endocrinology 141: 4056-4064.

Schmidt et al.; "The cytomegalovirus Enhancer: a Pan-Active Control Element in Transgenic Mice"; (1990) Mol. Cell. Biol. 10:4406-4411.

Stief et al.; "A nuclear DNA attachment element mediates elevated and position-independent gene activity"; (1989) Nature 341:343-5.

Wang et al.; "Thyroid Hormone-induced Gene Expression Program for Amphibian Tail Resorption"; (1993) J. Biol. Chem 268 22:16270.

Xu et al.; "Detection of programmed cell death using fluorescence energy transfer"; (1998) Nucleic Acids Research 26:2034-2035.

Searle, Peter, et al.; "Building a Metal-Responsive Promoter with Synthetic Regulatory Elements"; Mol. Cell. Biology; 5: 1480-1489; 1985.

Denver, Robert, et al.; "Thyroid Hormone-dependent Gene Expression Program for *Xenopus* Neural Development"; J. Biol. Chem 272:8179-88; 1997.

Farsetti, Antonella, et al.; "Characterization of Myelin Basic Protein Thyroid Hormone Response Element and Its Function in the Context of Native and Heterologous Promoter"; J. Biol. Chem.; 267:15784-8; 1992.

Furlow, David, et al.; "In Vitro and In Vivo Analysis of the Regulation of a Transcription Factor Gene by Thyroid Hormone during *Xenopus laevis* Metamorphosis"; Mol. Endocrinol. 13: 2076-89; 1999.

Hu, Mickey, C.-T.; et al.; "The Inducible *lac* Operator-Repressor System is Functional in Mannalian Cells"; Cell; 48:555-556; 1987.

Nover, L.; "Heat Shock Response"; e.d.; Boca Raton, Fla. pp. 167-220; 1991.

Gossen, M., et al.; Tight Control of gene expression in mammalian cells by tetracycline-responsive promoters. Proc. Natl. Acad. Sci.; vol. 89, pp. 5547-5551, Jun. 1992.

Fini et al., "An In Vivo Multiwell-Based Fluorescent Screen for Monitoring Vertebrate Thyroid Hormone Disruption," *Environ. Sci. Technol.*, 2007, vol. 41, pp. 5908-5914.

* cited by examiner

+T3 10nM

SEQUENCE LISTING

```
<160> NUMBER OF SEQ ID NOS: 12

<210> SEQ ID NO 1
<211> LENGTH: 20
<212> TYPE: DNA
<213> ORGANISM: Rattus sp.

<400> SEQUENCE: 1
ttggggttag gggaggacag                                              20

<210> SEQ ID NO 2
<211> LENGTH: 20
<212> TYPE: DNA
<213> ORGANISM: Xenopus sp.

<400> SEQUENCE: 2
ctagggttaa gtaaggtgaa                                              20

<210> SEQ ID NO 3
<211> LENGTH: 20
<212> TYPE: DNA
<213> ORGANISM: Xenopus sp.

<400> SEQUENCE: 3
ctaaggtaag cccgggttag                                              20

<210> SEQ ID NO 4
<211> LENGTH: 19
<212> TYPE: DNA
<213> ORGANISM: Xenopus sp.

<400> SEQUENCE: 4
```

-continued

| | | |
|---|---|---|
| gggcgaccta agaaggcag | | 19 |

<210> SEQ ID NO 5
<211> LENGTH: 20
<212> TYPE: DNA
<213> ORGANISM: Xenopus sp.

<400> SEQUENCE: 5

| | | |
|---|---|---|
| ggcaggtcat ttcaggacag | | 20 |

<210> SEQ ID NO 6
<211> LENGTH: 19
<212> TYPE: DNA
<213> ORGANISM: Xenopus sp.

<400> SEQUENCE: 6

| | | |
|---|---|---|
| gtctgacact gccgacctc | | 19 |

<210> SEQ ID NO 7
<211> LENGTH: 16
<212> TYPE: DNA
<213> ORGANISM: Xenopus sp.

<400> SEQUENCE: 7

| | | |
|---|---|---|
| aggtcagtta aggtga | | 16 |

<210> SEQ ID NO 8
<211> LENGTH: 14
<212> TYPE: DNA
<213> ORGANISM: Xenopus sp.

<400> SEQUENCE: 8

| | | |
|---|---|---|
| aggtgaacag gaca | | 14 |

<210> SEQ ID NO 9
<211> LENGTH: 16
<212> TYPE: DNA
<213> ORGANISM: Xenopus sp.

<400> SEQUENCE: 9

| | | |
|---|---|---|
| gggtacatat aggtca | | 16 |

<210> SEQ ID NO 10
<211> LENGTH: 1668
<212> TYPE: DNA
<213> ORGANISM: Gallus gallus

<400> SEQUENCE: 10

| | | |
|---|---|---|
| ggatccataa tataactgta ccaggttttg gtttattaca tgtgactgac ggcttcctat | | 60 |
| gcgtgctcag aaaacggcag ttgggcactg cactgcccgg tgatggtgcc acggtggctc | | 120 |
| ctgccgcctt ctttgatatt cactctgttg tatttcatct cttgttgccg atgaaaggat | | 180 |
| ataacagtct ctgaggaaat acttggtatt tcttctgatc agcgttttta taagtaatgt | | 240 |
| tgaatattgg ataaggctgt gtgtcctttg tcttgggaga caaagcccac agcaggtggt | | 300 |
| ggttgggtgg tggcagctca gtgacaggag aggttttttt gcctgttttt tttgttgttt | | 360 |
| ttttttttta agtaaggtgt tctttttttct tagtaaaatt tctactggac tgtatgtttt | | 420 |
| gacaggtcag aaacatttct tcaaaagaag aaccttttgg aaactgtaca gccctttttct | | 480 |
| ttcattccct ttttgctttc tgtgccaatg cctttggttc tgattgcatt atggaaaacg | | 540 |
| ttgatcggaa cttgaggttt ttatttatag tgtggcttga aagcttggat agctgttgtt | | 600 |

```
acatgagata ccttattaag tttaggccag cttgatgctt tattttttt cctttgaagt      660 agtgagcgtt ctctggtttt tttcctttga aactggcgag gcttagattt ttctaatggg     720 atttttacc tgatgatcta gttgcatacc caaatgcttg taaatgtttt cctagttaac      780
atgttgataa cttcggattt acatgttgta tatacttgtc atctgtgttt ctagtaaaaa     840
tatatggcat ttatagaaat acgtaattcc tgatttcctt ttttttttat ctctatgctc     900
tgtgtgtaca ggtcaaacag acttcactcc tatttttatt tatagaattt tatatgcagt     960
ctgtcgttgg ttcttgtgtt gtaaggatac agccttaaat ttcctagagc gatgctcagt    1020
aaggcgggtt gtcacatggg ttcaaatgta aacgggcac gtttgctgct gccttcccag     1080
atccaggaca ctaaactgct tctgcaactg aggtataaat cgcttcagat cccaggaagt    1140
gtagatccac gtgcatattc ttaaagaaga atgaatactt tctaaaatat gttggcatag    1200
gaagcaagct gcatggattt atttgggact taaattattt tggtaacgga gtgcataggt    1260
tttaaacaca gttgcagcat gctaacgagt cacagcattt atgcagaagt gatgcctgtt    1320
gcagctgttt acggcactgc cttgcagtga gcattgcaga taggggtggg gtgctttgtg    1380
tcgtgttggg acacgctgcc acacagccac ctcccgaaca tatctcacct gctgggtact    1440
tttcaaacca tcttagcagt agtagatgag ttactatgaa acagagaagt tcctcagttg    1500
gatattctca tgggatgtct ttttccat gttgggcaaa gtatgataaa gcatctctat      1560
ttgtaaatta tgcacttgtt agttcctgaa tcctttctat agcaccactt attgcagcag    1620
gtgtaggctc tggtgtggcc tgtgtctgtg cttcaatctt ttaagctt                 1668

<210> SEQ ID NO 11
<211> LENGTH: 1216
<212> TYPE: DNA
<213> ORGANISM: Gallus gallus

<400> SEQUENCE: 11
tctagaggga cagccccccc ccaaagcccc cagggatgta attacgtccc tcccccgcta      60
gggggcagca gcgagccgcc cggggctccg ctccggtccg gcgctccccc cgcatccccg     120
agccggcagc gtgcggggac agcccgggca cggggaaggt ggcacgggat cgcttttcctc    180 tgaacgcttc tcgctgctct ttgagcctgc agacacctgg ggggatacgg ggaaaaagct    240
ttaggctgaa agagagattt agaatgacag aatcatagaa cggcctgggt tgcaaaggag    300
cacagtgctc atccagatcc aaccccctgc tatgtgcagg gtcatcaacc agcagcccag    360
gctgcccaga gccacatcca gcctggcctt gaatgcctgc agggatgggg catccacagc    420
ctccttgggc aacctgttca gtgcgtcacc accctctggg ggaaaaactg cctcctcata    480
tccaacccaa acctcccctg tctcagtgta aagccattcc cccttgtcct atcaggggg    540 agtttgctgt gacattgttg gtctggggtg acacatgttt gccaattcag tgcatcacgg    600
agaggcagat cttggggata aggaagtgca ggacagcatg acgtgggac atgcaggtgt    660 tgagggctct gggacactct ccaagtcaca gcgttcagaa cagccttaag gataagaaga    720
taggatagaa ggacaaagag caagttaaaa cccagcatgg agaggagcac aaaaaggcca    780
cagacactgc tggtccctgt gtctgagcct gcatgtttga tggtgtctgg atgcaagcag    840
aaggggtgga agagcttgcc tggagagata cagctgggtc agtaggactg ggacaggcag    900
ctggagaatt gccatgtaga tgttcataca atcgtcaaat catgaaggct ggaaaagccc    960
tccaagatcc ccaagaccaa ccccaaccca ccaccgtgc ccactggcca tgtccctcag    1020
tgccacatcc ccacagttct tcatcacctc cagggacggt gaccccccca cctccgtggg   1080
```

-continued

```
cagctgtgcc actgcagcac cgctctttgg agaaggtaaa tcttgctaaa tccagcccga    1140
ccctcccctg gcacaacgta aggccattat ctctcatcca actccaggac ggagtcagtg    1200
aggatggggc tctaga                                                    1216

<210> SEQ ID NO 12
<211> LENGTH: 836
<212> TYPE: DNA
<213> ORGANISM: Xenopus laevis

<400> SEQUENCE: 12
gatctccctg ctctttataa aatgactgaa tgtctccctg ttgtgtataa tggtgcagag      60
tatgttatgg ttgctaatag actgagctgt tatatagagg cagagggaca tgttgatagg     120
ctgtgcattc agtacacatg agtagcgagt gccgttcagg agttgagaga ggggagaggg     180
aggcttgggg agttgtgagc aagagaaggg gacagagtga gtgagaggag gggaaaggct     240
ggcacatttt cacaggacgc actagggtta agtaaggtga atgctcagcc tcatttgaac     300
tctgtagggt tgggagagac acacacgctg tgtatataca tagtgataga gagagggggc     360
cgggagcgag acagggctg gggagagttc agcacaggag agagaggcag ggagagggac     420
aaagagacac ttagcaacag ggatcagctt ggggacaagt gagaagcaag agcaagttct     480
gctgcccatt caggtatagt ataacctgca atctgcatgc aactgccatg tactcccact     540
cccacctctc ttctactgca tatacactga tagcacagcc tagtctgctg agcttacact     600
ctaatataca gtgagacaca gatacaatac agggagagga actattggga gaagagaata     660
ctgctctgca aagcttacac tccattatac agagggacac agatacaata cagagaggga     720
accattggta gaagagagta ctgccctgca gagcttacac tctagtgtac aggcggacac     780
ataaacactt catggaaatg ggagcaaatt aggtaaagaa tagatttcag aaagat         836
```

TRANSGENIC CLAWED FROG EMBRYOS AND USE THEREOF AS DETECTORS OF ENDOCRINE DISRUPTERS IN THE ENVIRONMENT

This application is a 371 of International Application No. PCT/FR03/01598, filed May 27, 2003, which claims priority to French foreign application 02/06669, filed May 30, 2002, the contents of which are incorporated herein by reference The present invention relates to the field of biology, and more particularly of animal transgenesis. More particularly, the present invention relates to transgenic frogs, in particular at the tadpole stage, or the cells derived therefrom, and also to their use in methods intended to identify the presence of endocrine disrupters in the environment, such as molecules that are nuclear receptor agonists or antagonists.

A large variety of chemical compounds diffuse widely in the natural environment. Among these, there are many which have effects of the hormonal type, which are undesirable due to their physicochemical properties. The presence of hormonal pollutants in natural water is thus revealed through the observation of fertility problems in various aquatic species. In fact, several current research approaches confirm the presence of endocrine disrupters in our environment.

Substances that disrupt the endocrine system mimic the biological effects of hormone factors (estrogens, androgens and thyroid hormones) which finely regulate many functions such as the functions of homeostasis, of reproduction, of development or of behavior. These substances of natural or synthetic origin are in fact recognized by a living organism as molecular factors involved in the processes regulated by hormones and therefore interfere with the action of hormones.

The widespread presence of these factors is causing the attention of governmental authorities to be drawn throughout the world and is bringing about the need for large companies to take into account the environmental impact of their activities. In response to these problems, it is necessary, or even legally stipulated, to test any chemical product or industrial waste from the point of view of their hormonal activities.

It is therefore crucial to set up a reliable evaluation, based on the production of integrated models, that gives sensitive, rapid, quantifiable and tissue-specific results, and that is very flexible to use, for detecting environmental endocrine disrupters. This is the problem that the present invention proposes to solve by providing transgenic aquatic organisms, preferably at the embryonic stage and therefore transparent, in the cells of which organisms the expression of a reporter protein is finely modeled by the presence of factors that disrupt hormone function. In addition, the present invention allows, through combining several reporter, preferably fluorescent, proteins, the simultaneous and early measurement, in the same animal, of various pollutants. According to the gene construct used, it is also possible to detect effects specific for a tissue (neurotoxic effects, hepatotoxic effects, etc.).

The present invention therefore relates to a transgenic cell from an aquatic animal selected from amphibians and teleosts, comprising at least one expression cassette, said cassette comprising a regulatory DNA sequence, preferably from vertebrates, selected from nuclear hormone receptor response elements, functionally linked upstream of a DNA segment encoding a reporter protein, and optionally a polyadenylation signal and optionally an "insulator" sequence at each end of said cassette. According to one embodiment, said cassette also comprises a minimum promoter sequence.

For the purpose of the present invention, the term "transgenic" is intended to denote a cell, or an animal comprising at least one cell, comprising a transgene. The term "transgene" or the expression "exogenous nucleic acid sequence", or the term "exogenous gene" or the term "expression cassette", terms which will be used without distinction in the present application, is intended to note genetic material which has been or which will be inserted artificially into the genome of an animal, particularly into an animal cell that is cultured in vitro or into a cell of a living animal, or which will be maintained in said cell in episomal form. Preferably, the transgene according to the present invention comprises at least one sequence capable of being transcribed or transcribed and translated into a protein.

Preferably, but nonexhaustively, the nuclear hormone receptor response elements are chosen from the estrogen response element (ERE) (Mader et al. 1993), the thyroid hormone response element (TRE), the glucocorticoid response element (GRE) and the mineralocorticoid response element (MRE) (Kolla et al. 1999), the progesterone response element (PRE) (Hecht et al. 1988) and the vitamin D response element (DRE) (Kitazawa et al. 2002).

According to a first preferred embodiment of the invention, the nuclear hormone receptor response element is TRE. Various regulatory sequences containing TREs can be used in the present invention; for example, the TRE sequence of the rat malic enzyme (Seq ID No. 1), one copy of the DR4 consensus TRE sequence (Seq ID No. 5; Seq ID No. 6), three copies of the consensus TRE sequence (DR4)X3, the DR4 sequences being 4 nucleotides apart. According to a second preferred embodiment of the invention, the nuclear hormone receptor response element is ERE.

The expression "regulatory sequence or regulatory elements for the expression of the gene" is intended to denote all the DNA sequences involved in the regulation of gene expression, i.e. essentially the regulatory sequences for transcription, for splicing and for translation. Among the regulatory DNA sequences for transcription, mention should be made of the minimum promoter sequence, the upstream sequences (for example, the nuclear hormone receptor response elements such as TRE, ERE, GRE, etc.), the activating sequences (enhancers), optionally the inhibiting sequences (silencers), the insulating sequences (insulators), such as the MARs (matrix attachment regions) (Seq ID No. 10, No. 11), and the splicing sequences. The regulatory DNA sequence according to the invention is preferably a vertebrate sequence, preferably a *xenopus* or teleost sequence, and more preferably a human sequence.

These expression-regulating sequences are functionally linked to the reporter gene(s). A nucleic acid sequence is "functionally linked" when it is placed in a functional relationship with another nucleic acid sequence. For example, an upstream promoter or regulatory sequence is functionally linked to a coding sequence if it modulates or affects the transcription of said coding sequence. As regards the regulatory sequences for transcription, the term "functionally linked" signifies that the DNA sequences linked are contiguous and, when this involves linking two coding regions for proteins, they are contiguous and in reading frame.

The expression "minimum promoter sequence" is intended to denote a promoter which, devoid of its upstream regulatory sequences, is capable of inducing the transcription of the gene, to which it is functionally linked, at a baseline level. By way of example of a minimum promoter, mention should be made of the promoter of the herpes simplex virus thymidine kinase gene, the promoter of the simian cytomegalovirus (simian CMV IE94) and the adenoviral E1b promoter (Argenton et al. 1996).

The promoter and regulatory sequences according to the invention are defined according to the desired expression profile for the reporter protein. Preferably, the reporter gene is placed under the control of tissue-specific or cell-specific or ubiquitous expression elements.

The tissue-specific expression elements or tissue-specific promoters are chosen from the promoters which make it possible to obtain a specific, and preferably strong, expression in one or more cell(s), tissue(s), cell type(s) or organ(s) of the aquatic animal according to the invention. These promoters may or may not be heterologous for the organism and may or may not be naturally present in the genome of the organism. The tissue-specific promoters according to the invention are preferably chosen from the sequences which direct expression in the liver, the central nervous system, in particular the hypothalamus, and the osteoblasts. The expression in the liver is particularly advantageous given that the environmental pollutants are concentrated in this detoxifying organ. In this respect, mention may be made of the promoters of the genes:

for vitellogenin, CYP26, CYP3A which direct expression of the gene in the liver. The promoter of the *xenopus* and chicken vitellogenin gene is an example of a tissue-specific promoter. The expression of this gene in the liver is induced by estrogens. The *xenopus* vitellogenin A2 gene contains an estrogen response element between −331 and −319. The chicken vitellogenin gene contains various response elements for hormones, such as glucocorticoids, estrogens and progestins, located between −721 and −591 bp;

the promoter of stromelysin 3 which encodes an enzyme that participates in the remodeling of the extracellular matrix that is expressed in the limb buds, in the intestine during metamorphosis, and in certain tissues during remodeling (Ishizuya-Oka et al. 1996);

for vasopressin, BTEB, TH/bZIP which directs expression of the gene in the brain. Vasopressin is a neurohypophyseal hormone involved in the metabolism of water and the regulation of blood pressure; it is also involved in neurotransmission and neuromodulation in the central nervous system. The expression of this gene is regulated by estrogens and testosterone. The promoter sequence of rat vasopressin contains two estrogen response elements (EREs) located in a 1.5 kbp distal fragment (Shapiro et al., 2000). The promoter of the BTEB (basic transcription element-binding) gene constitutes another example of a tissue-specific promoter (Denvers et al., 1997). The BTEB gene is expressed in the brain and its expression is induced by the Tri-iodothyronine (T3)-thyroid hormone in vivo (Denvers et al., 1999). A part of the promoter of the *xenopus* BTEB gene has been cloned (Brown et al., 1996). Another example of a tissue-specific promoter consists of the promoter (Seq ID No. 12) of the TH/bZIP gene which encodes a basic leucine zipper transcription factor (Wang et al., 1993). The expression of the TH/bZIP gene is effectively regulated by exogenous thyroid hormones and at the time of metamorphosis in *xenopus*, which is a thyroid hormone-dependent process (Furlow et al., 1999). The portion of promoter of the TH/bZIP gene between −246 bp and +130 bp contains two TREs (Seq ID No. 2 and No. 3);

Cbf1 which encodes a transcription factor specifically expressed in osteoblasts (Kasenty et al., 2000). The expression of this factor, which plays a determining role in osteoblast differentiation and function, is induced by estrogens and its promoter contains an ERE.

In the context of a multitransgenic cell or animal according to the invention, it is possible to simultaneously analyze a positive or negative regulation of the expression of the reporter gene. For example, the TSH (thyroid stimulating hormone) promoter upstream of GFP is positively regulated by the T3 hormone, whereas the TRH (thyrotropin releasing hormone) promoter is negatively regulated by T3. Thus, a cell comprising the "TSH promoter/GFP" and "TRH promoter/RFP" expression cassettes would make it possible to identify or to screen compounds that act positively or negatively on the gene expression.

The article by Metzger and Feil (1999) gives, by way of nonlimiting example (cf. table on page 471), a list of tissue-specific promoters which can be used for directing the expression of the reporter protein in various tissues. The tissue-specific promoters are, more generally, chosen from those which direct the expression of the reporter protein in a physiological system, an organ, a tissue, a cell type or a particular cell, among which, mention should be made, nonexhaustively, of the central nervous system in general, and in particular the brain, the cerebellum, neurons, motoneurons, glial cells, Schwann cells, the hypophysis, the hypothalamus, the pituitary gland, the hippocampus and the cortex, the heart, ventricular cardiomyocytes and atrial cardiomyocytes, the lungs, the bones, the eyes, and more particularly the retina and the crystalline lens, the skin, and more particularly the dermis and the epidermis, the muscles, and more particularly the skeletal muscles, the cardiac muscle and the smooth muscles, the mammory gland, the gonads, and more particularly the testes, the ovaries, the germinal cells, the oocytes, the oogonia, the spermatozoa, the spermatogonia and the spermatocytes, the kidney, the liver and in particular the hepatocytes, the spleen, the pancreas and in particular the Langerhans cells and the β-cells, the tongue, the esophagus, the adipose tissue, and the endothelial cells.

The ubiquitous expression elements or ubiquitous promoters are chosen from the promoters which make it possible to obtain expression, preferably strong expression, in all or, at least, in a large proportion of organs or of tissues of the organism according to the invention. These promoters may or may not be heterologous with respect to the organism according to the invention. By way of nonlimiting example of ubiquitous promoters, mention may be made of the cytomegalovirus (CMV) promoter (Schmidt et al., 1990) and the interferon-inducible promoter (Mx1) (Hug et al., 1998; Arnheiter et al., 1990). In addition, the expression elements or promoters according to the invention may provide a constitutive or inducible control of the expression of the fusion gene. Among the elements providing inducible expression, mention should be made of the eukaryotic promoters inducible by heavy metals (Mayo et al., 1982; Brinster et al., 1982; Seark et al., 1985), by a thermal shock (Nover et al., 1991), by hormones (Lee et al., 1981; Hynes et al., 1981; Klock et al., 1987; Israel et al., 1989), or by interferon (Hug et al., 1998; Arnheiter et al., 1990). Mention should also be made of the inducible prokaryotic expression elements, such as the Lac repressor system (LacR/operator/inducer) of *E. coli* (Hu et al., 1987; Brown et al., 1987; Figge et al., 1988; Deuschle et al., 1990; Labow et al., 1990), or the tetracycline-resistant system of *E. coli* (Gossen et al., 1992) (WO 94 04 672, EP 804 565).

Said reporter protein is selected from the group of autofluorescent proteins and enzymes detectable by a histochemical method. Preferably, said fluorescent protein is chosen from the group composed of the green fluorescent protein (GFP), the enhanced green fluorescent protein (EGFP), the red fluorescent protein (CFP and Red FP, RFP), the blue fluorescent protein (BFP), the yellow fluorescent protein (YFP), and the fluorescent variants of these proteins, the fluorescent proteins that change color with time ("fluorescent Timer™ sold by Clonetech"), fluorescent proteins for which the fluorochromes have a very short lifetime, and fusion proteins, such as the luciferase/GFP fusion protein made up of at least two fluorescent proteins, and which allow a visual and quantitative analysis. Among the fluorescent proteins used, the fluorescent timer protein is particularly preferred, since the change from green fluorescence to a red fluorescence reflects the activity of the promoter which directs the expression of this reporter protein. It is thus possible to evaluate the persistence of a compound or of a pollutant on the activity of the promoter, after contact of the animal or of the cell according to the invention with the pollutant. The use of such a type of reporter protein thus makes it possible to evaluate the dynamics of activation of a promoter. According to another type of embodiment, it is advantageous to use proteins for which the fluorescence has a short lifetime. Thus, the cells and the animals will be examined immediately after the contact with the pollutant(s) has been terminated. Disappearance of the fluorescence or its persistence after a period of time longer than that of the half-life of the fluorochrome will indicate whether the promoter(s) is (are) still activated. According to another type of embodiment, it is advantageous to use a reporter gene encoding a fusion protein made up of two different fluorescent proteins combined by means of a linker peptide which contains a caspase-3 recognition site (Xu et al., 1998 and Luo et al., 2001). Thus, the sequences encoding GFP and BFP, respectively CFP and YFP, have been combined by means of an 18 amino acid peptide containing a cleavage sequence specific for caspase 3, which is one of the effector proteins of programmed cell death. There is an energy transfer between the two fluorophores as long as the caspase-3 proteases are not activated. Entry of the cells into apoptosis activates the caspase-3 proteases, resulting in cleavage of the fusion protein and termination of the energy transfer, and therefore visibility of the GFP, respectively of the CFP. Such a transgenic cell or animal therefore makes it possible to detect the effect of the pollutant on the phenomenon of apoptosis. The use of transgenic cells or animals comprising two reporter genes encoding the autofluorescent fusion proteins GFP/BFP and CFP/YFP makes it possible to simultaneously obtain the same type of information regarding any possible toxicity of two distinct categories of pollutants (estrogens and thyroid hormones, for example). Such transgenic cells or animals are particularly useful in the case of two transgenes that respond to different hormonal types but that are expressed in the same tissues or else are expressed ubiquitously.

According to another embodiment, the enzyme that is detectable by a histochemical method is chosen from the group composed of luciferase, β-galactosidase, β-glucuronidase, alkaline phosphatase, chloramphenicol acetyl transferase, and alcohol dehydrogenase. According to a preferred embodiment, it is luciferase. The term "luciferase" is intended to denote all the proteins which catalyze or initiate a bioluminescent reaction in the presence of a substrate called luciferin. The luciferase according to the invention may come from many organisms or systems that generate bioluminescence (see U.S. Pat. No. 6,152,358). For example, the luciferase according to the invention may come from Renilla (U.S. Pat. No. 5,418,155 and U.S. Pat. No. 5,292,658) or from *Photinus pyralis* or from *Luciola cruciata* (U.S. Pat. No. 4,968,613).

The recombinant DNA technology used for constructing the expression cassette or the expression vector containing it is that which is known and commonly used by those skilled in the art. Standard techniques are used for the cloning, the DNA isolation, the amplification and the purification; the enzyme reactions involving DNA ligase, DNA polymerase and restriction endonucleases are carried out according to supplier's recommendations. The vectors include plasmids, cosmids, phagemids, bacteriophages, retroviruses and other animal viruses, artificial chromosomes, such as YACs, BACs or HACs, and other similar vectors. These techniques and the others are generally carried out according to Sambrook et al. (1989 Molecular cloning: a laboratory manual second edition—Cold Spring Harbor Laboratory Press. Cold Spring Harbor, N.Y. USA).

The present invention also covers the expression cassette or transgene according to the invention, and also the vectors containing it. In fact, the transgene can be cloned into a cloning vector which makes it possible to provide the propagation thereof in a host cell, and/or optionally into an expression vector for providing expression of the transgene.

The methods for generating transgenic cells are well known to those skilled in the art. The expression cassette or the transgene according to the invention, optionally included in a linearized or nonlinearized vector, or in the form of a vector fragment, can be introduced into the host cell by standard methods such as, for example, microinjection into the nucleus (U.S. Pat. No. 4,873,191), transfection by calcium phosphate precipitation, lipofection, electroporation, thermal shock, transformation with cationic polymers (PEG, polybrene, DEAE-dextran, etc.), viral infection, or sperm (Kroll and Amaya, 1996). Kroll and Amaya (1999) have more particularly described a method for generating transgenic frog embryos. In order to screen the cells into which at least one transgene has been introduced, positive and/or negative markers, also called selection genes, can be inserted into the vector. Various systems for selecting cells have been described; mention should be made of the system described which uses positive/negative selection vectors (Capecchi et al., 1989).

According to a first embodiment, the cell according to the invention comprises an expression cassette comprising, sequentially in the 5'-3' direction, the rat malic enzyme TRE sequence (Seq ID No. 1), the minimum promoter of the herpes simplex virus thymidine kinase (TK) gene, functionally linked to a DNA segment encoding the enhanced green fluorescent protein, a polyadenylation signal and, optionally, an "insulator" sequence at each end of said cassette (Seq ID No. 10 or Seq ID No. 11).

According to a second embodiment, the cell according to the invention comprises, sequentially in the 5'-3' direction, the promoter sequence of the *xenopus* stromelysin 3 gene comprising several TREs (Seq ID No. 7, Seq ID No. 8, Seq ID No. 9), functionally linked to a DNA segment encoding luciferase, a polyadenylation site and, optionally, an "insulator" sequence at each end of said cassette (Seq ID No. 10 or No. 11).

According to a third embodiment, the cell according to the invention comprises, sequentially in the 5'-3' direction, the rat malic enzyme TRE sequence (Seq ID No. 1), the minimum promoter of the herpes simplex virus thymidine kinase (TK) gene, functionally linked to a DNA segment encoding luciferase, a polyadenylation signal and, optionally, an "insulator" sequence at each end of said cassette (Seq ID No. 10 or No. 11).

The aquatic animal cell and/or the nonhuman transgenic animal according to the invention is obtained by introducing at least one expression cassette encoding a reporter protein into a cell, a zygote or an early embryo of the animal. The introduction of various transgenes into the cell according to the invention can also be carried out simultaneously or in a manner spread out over time. When the cell is multitransgenic, then the transgenes preferably each encode a distinct reporter protein, and the expression of each reporter protein is specific for an environmental pollutant type.

The cell according to the invention comprises at least one transgene according to the invention, present either in the form of an extrachromosomal element, or stably integrated into the chromosomal DNA in a random or targeted manner. When several transgenes are present in the cell according to the invention, they may be present in the form of an extrachromosomal element and/or stably integrated into the chromosomal DNA in a random or targeted manner.

According to a preferred embodiment, the expression cassette is integrated stably into the chromosomal DNA in a random or targeted manner. The term "stably integrated" is intended to mean insertion of the transgene into the genomic DNA of the cell according to the invention. The transgene thus inserted is then transmitted to the cell progeny.

According to another embodiment of the invention, the cell is characterized in that said expression cassette or transgene encoding at least one reporter protein is present in episomal form in said cell. It is within the scope of those skilled in the art to define the nature and the characteristics of the expression vector used for maintaining and expressing the transgene, in episomal form, in the cell of the invention.

In the germinal transgenesis context, all the cells of the animal, and in particular its germinal line cells, are transgenic. In this case, the expression cassette is preferably integrated stably into the chromosomal DNA in a random or targeted manner. When the integration of the reporter gene is targeted by homologous recombination in the genome of the organism ("knock-in"), the reporter gene may be devoid of promoters and/or of expression elements and may be placed under the control of an endogenous promoter or of endogenous expression elements.

In the somatic transgenesis context, only some of the cells of the animal are transgenic, at the site of injection of the transgene. In this case, the expression cassette or transgene is preferably present in episomal form in the cell.

The cell according to the invention is preferably a cell from an amphibian, preferably the frog, selected from *Xenopus laevis* and *Xenopus tropicalis*. Given the genetic polymorphisms present in the population, it may be advantageous, in order to analyze or obtain a characteristic physiological or behavioral response, for the transgenic amphibians according to the invention, and in particular the transgenic frogs according to the invention, to have different genetic backgrounds such as the species *Xenopus laevis* and *Xenopus tropicalis*. According to another embodiment, the cell according to the invention is a teleost cell, preferably a zebra fish cell or a medaka cell.

The present invention also relates to a nonhuman transgenic aquatic animal selected from amphibians and teleosts, comprising at least one cell according to the invention as described above. When this animal is an aquatic/terrestrial animal such as amphibians or batrachians, it is selected from the Anura, the Urodela and the Apoda. They are preferably Anura, more preferably clawed frogs of the families pipidae and ranidae. The clawed frogs are preferably selected from *Xenopus laevis* and *Xenopus tropicalis*. According to a second embodiment of the invention, the animal is a teleost. The term "teleosts" is intended to denote "bony" fish, i.e. their skeleton is completely ossified. The teleost group includes, for example, the zebra fish, the medaka, the giant rerio and the puffer fish.

The aquatic animals of the present invention have a certain number of advantages compared with the conventional animal model systems such as mice, *drosophila* or nematodes. First of all, *xenopus* and the teleosts are, from an evolutionary point of view, closer to humans and, in this respect, the screening model of the present invention is much more relevant. The molecular and morphological bases of tissue and organ development are either identical or similar to the other vertebrates, including humans. The second advantage provided by the aquatic animal models of the present invention is that their embryos are very transparent. Given the transparency of the embryos, the activity of the compounds administered to or brought into contact with the animal can be detected and diagnosed much more rapidly than in nontransparent animals. These activities can be detected essentially only at the embryonic stage in *xenopus*. Another advantage of these aquatic animals is that they develop rapidly compared with animals such as mice. The aquatic animals according to the invention also have the advantage that the test compounds can be administered directly to the animal undergoing development, which is not the case for animals which develop in vitro. Finally, another not insignificant advantage of the choice of the aquatic animal according to the invention is the cost of maintenance and of breeding, which is low compared to that generated by animals such as mice. Finally, given the small size of the *xenopus* or zebra fish embryo, the system according to the invention is very suitable for the use of multiwell microplates for the detection in large quantity of the expression of the reporter gene, and thus allows this detection to be automated.

More particularly, the invention covers a transgenic frog and its progeny, at the various stages of their development, and preferably at the tadpole stage, obtained by germinal transgenesis, characterized in that all the cells of the animal are transgenic. The expression "various stages of development" is intended to denote the zygote, the tadpole and the adult frog.

According to another embodiment, the invention covers the transgenic frog, at the various stages of its development, and preferably at the tadpole stage, obtained by somatic transgenesis, characterized in that some of the cells of said animal are transgenic.

It is obvious that the transgenic animal according to the invention can comprise transgenic cells derived from germinal transgenesis and transgenic cells derived from somatic transgenesis.

More preferably, the transgenic frog according to the invention is at the tadpole stage. According to a first embodiment, the invention covers a transgenic tadpole comprising at least one cell comprising an expression cassette comprising, sequentially in the 5'-3' direction, the promoter sequence of the *xenopus* stromelysin 3 gene comprising several TREs (Seq ID No. 7, No. 8, No. 9), functionally linked to a DNA segment encoding luciferase, a polyadenylation signal and, optionally, an "insulator" sequence at each end of said cassette. According to a second embodiment, the invention covers a transgenic tadpole comprising at least one cell comprising a DNA expression cassette comprising, sequentially in the 5'-3' direction, the rat malic enzyme TRE sequence (Seq ID No. 1), the minimum promoter of the herpes simplex virus thymidine kinase (TK) gene, functionally linked to a DNA segment encoding luciferase, a polyadenylation sequence and, optionally, an "insulator" sequence at each end of said cassette. According to a third embodiment, the invention covers a transgenic tadpole comprising at least one cell comprising a DNA expression cassette comprising, sequentially in the 5'-3' direction, the rat malic enzyme TRE sequence (Seq ID No. 1), the minimum promoter of the herpes simplex virus thymidine kinase (TK) gene, functionally linked to a DNA segment encoding the enhanced green fluorescent protein, a polyadenylation signal and, optionally, an "insulator" sequence at each end of said cassette.

One of the objects of the present invention is also to provide a method for identifying the presence of at least one environmental pollutant which modulates, i.e. inhibits or stimulates (preferably stimulates), transcription mediated by nuclear hormone receptor response elements, comprising the steps of:
  a) bringing a cell or an animal according to the invention into contact, in an aqueous medium comprising the environmental pollutant;
  b) bringing a cell or an animal according to the invention into contact in the aqueous medium;
  c) qualitatively, optionally quantitatively, determining the expression of the reporter protein in a) and b) and then comparing said expressions;
such that a difference in expression of said reporter protein in a) and b) indicates the presence of environmental pollutants in the medium. The method is characterized in that a distinct reporter protein corresponds to each type of environmental pollutant.

An object of the present invention is also to provide a method for screening (a) compound(s) which modulate(s), i.e. inhibit(s) or stimulate(s) (preferably stimulate(s)) transcription mediated by nuclear hormone receptor response elements, comprising the steps of:
  a) bringing a cell or an animal according to the invention into contact, in an aqueous medium comprising the compound(s);
  b) bringing a cell or an animal according to the invention into contact, into said aqueous medium;
  (c) qualitatively, optionally quantitatively, determining the expression of the reporter protein in a) and b) and then comparing said expressions;
  (d) selecting the compound(s) that induce(s) a difference in expression of said reporter protein in a) and b).

The screening method according to the invention may also comprise the step of somatic transfer, into the cell or into at least one transgenic cell of the animal according to the invention, of at least one nuclear hormone receptor gene. In fact, the addition of a transgene overexpressing at least one nuclear hormone receptor in a cell of the animal according to the invention makes it possible to increase the sensitivity of detection when the methods of the invention are carried out. Such transgenes comprise tissue-specific or ubiquitous promoters for directing the expression of said receptor at the appropriate sites.

The method according to the invention is also intended for the simultaneous screening of at least two compounds, characterized in that a distinct reporter protein corresponds to each compound.

The method according to the invention is particularly useful for determining whether a known compound is capable of being an endocrine disrupter. In practice, the test compound liable to have an effect on transcription mediated by nuclear hormone receptor response elements is brought into contact with the cell or the aquatic animal by directly adding said compound to the aqueous medium containing the living cell or animal. In practice, if it is a cell, said test compound(s) is (are) placed in the culture medium. If it is an animal, in particular a tadpole, the test compound(s) is (are) placed in the aqueous medium in which the animal is living. Alternatively, if it involves detecting the presence of compounds in the water of a river, of a lake or of any other natural aquatic medium in which the presence of environmental contaminants is suspected, the animal is placed in this aquatic medium. In this case, the aqueous medium serving as a control for carrying out step b) of the methods according to the invention may be the water from the river, from the lake or from any other natural aquatic medium which may or may not be treated and not containing the test compound or the compound to be screened. Such approaches are used for introducing chemical agents into fish embryos (M. Westerfield, The zebrafish book: a guide for the laboratory use of zebrafish $3^{rd}$ Ed., 1995). Alternatively, the compounds may be administered to the aquatic animals according to the invention by electroporation, lipofection or ingestion. Alternatively, the compound(s) to be screened or to be detected can be directly brought into contact with the cell or the animal according to the invention by injecting it or them directly into the living cell or animal. For example, the compound may be injected into the brain or the dorsal muscle of a tadpole.

The compound to be screened or to be studied can be administered alone or in conjunction with other compounds or solvents or transporters. The compound may be brought into contact with the animal simultaneously, at the same time or after the administration of the reagent or of the colorant used for detecting the expression of the reporter gene.

It may be advantageous, before carrying out the methods according to the invention, to pretreat the cells or animals according to the invention in order to increase their sensitivity to the compounds to be screened, detected or measured. Thus, the inventors have developed a method of treatment based on perchlorate. The animals or cells are treated with perchlorate for a period of time which can range up to one month, at approximately 1 g/l in the aquatic medium or the culture medium, respectively. The animals or cells are then sensitized to the compounds (if it is known).

The compounds which can be screened by means of the method according to the invention are extremely varied and are characterized by their ability to directly or indirectly bind the nuclear hormone receptor. Said compound may thus compete with said nuclear receptor for its binding to the nuclear hormone receptor response elements (REs), or else with the receptor ligand, i.e. the hormone. The compounds are molecules that are agonists or antagonists of nuclear receptors such as the thyroid hormone receptor (TR), the estrogen receptor (ER), the retinoic acid receptor (RAR), the glucocorticoid receptor (GR), the mineralocorticoid receptor (MR), orphan receptors or the vitamin D receptor. The term "compound" includes any element, entity or agent including, without any limitation or exhaustive nature being implied, pharmaceutical, therapeutic, pharmacological, chemical, environmental, agricultural, aquatic or cosmetic pollutants or compounds, drugs, medicinal products, and natural or synthetic products. For example, according to a preferred embodiment, said screened compound has an osteoprotective effect devoid of adverse uterotrophic effects, and therefore constitutes a pharmaceutical agent.

The techniques and means for detecting the expression of the reporter gene(s) are well known to those skilled in the art. They comprise, nonexhaustively, the human eye, photographic film, a photomultiplier, a photodiode (for review see U.S. Pat. No. 5,571,722). The detection means may also comprise a measuring device and/or a computer for storing the data and calculating the level of expression of the reporter gene and, by comparison with a standard, calculating the concentration of said compound or environmental pollutant in the medium. More generally, the means for detecting bioluminescence measure the intensity of the light as a function of the concentration of compounds or environmental pollutants.

The invention relates to the use of the method according to the invention, for analyzing and studying the mode of biological action of (a) compound(s) which modulate(s) transcription mediated by nuclear hormone receptor response elements. The invention also relates to the use of the method according to the invention, for studying the dose effect of the environmental pollutants which stimulate transcription mediated by nuclear hormone receptor response elements.

More generally, an object of the present invention is to use a cell and/or an animal according to the invention, for detecting, analyzing and/or studying the environmental contaminants, in particular in water. The invention is particularly useful for analyzing and/or evaluating the quality of water.

Another use of the cell and/or of the animal according to the invention lies in the study of toxicity and/or of toxicology, in particular in cosmetology, in agrochemistry or in pharmacy. Thus, the present invention is particularly useful in a FETAX study protocol.

The transgenic cells and animals according to the invention are also particularly useful for detecting, studying and measuring the cell lethality induced by certain compounds, the teratogenicity and the tumorigenicity of certain compounds, and also the pro-apoptotic properties of certain compounds.

The invention is also directed toward protecting a device for detecting environmental pollutants, in particular in water, and/or (a) compound(s) which modulate(s) transcription mediated by nuclear hormone receptor response elements, characterized in that it comprises at least one cell and/or at least one animal, preferably a *xenopus* at the tadpole stage or a zebrafish, according to the invention, and, optionally, means for detecting the expression of the reporter gene(s).

Other characteristics and advantages of the present invention will be demonstrated more clearly on reading the following examples. In these examples, reference will be made to the following figures.

FIGURES

FIG. 1: Diagrammatic representation of the promoter of the TH/bZIP gene and of the position of the primers for isolating, by PCR, the DNA fragment containing the two thyroid hormone response elements (TREs). The 410 bp amplification product is visualized on agarose gel.

Figure 2:

FIG. 2: Diagrammatic representation of an expression cassette containing a promoter sequence containing TREs (thyroid response elements).

Figure 3:
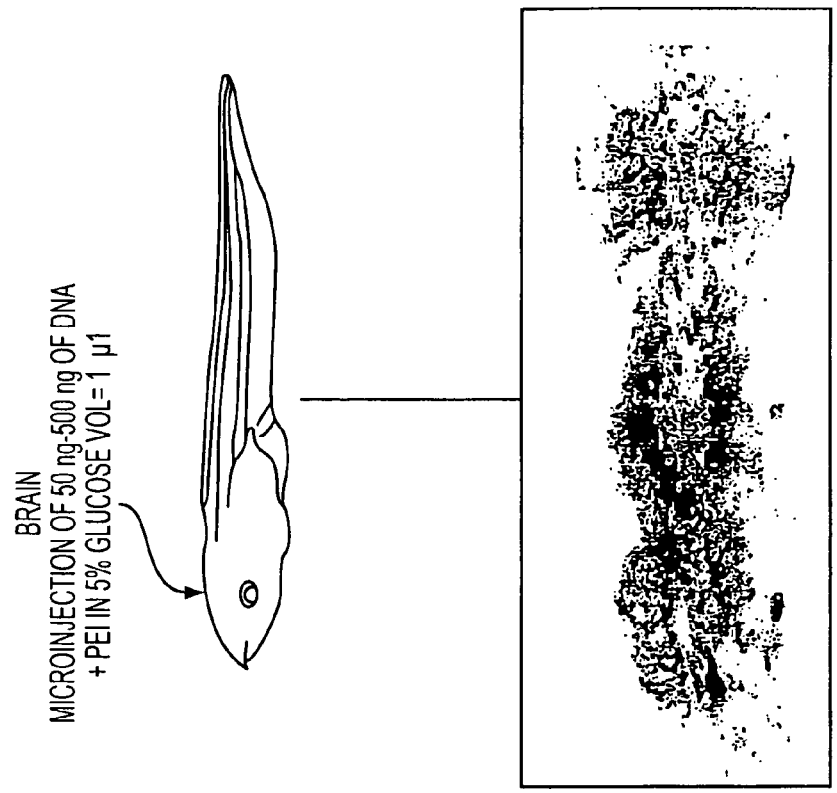
Figure 3:
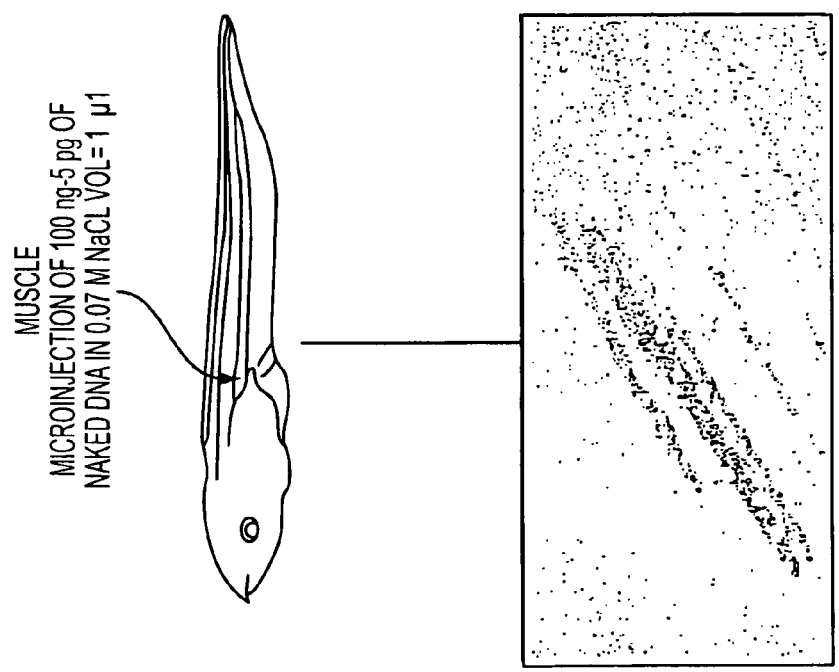

FIG. 3: Somatic transgenesis in the muscle (on the left) and in the brain (on the right). In the muscle, the DNA is introduced into the cells by microinjection of naked DNA. In the brain, the DNA is complexed with polyethyleneimine (PEI), and then microinjected into the brain.

Figure 4:
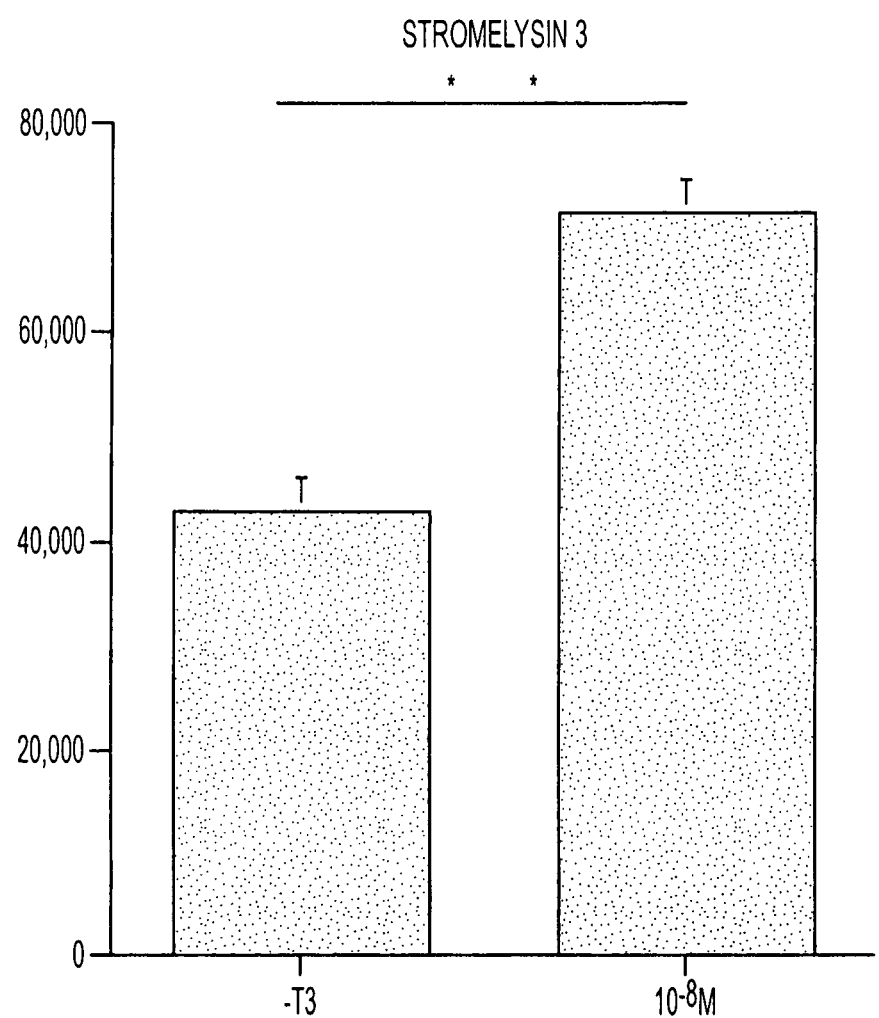

FIG. 4: Assay for functionality of the construct "*xenopus* stromelysin 3 promoter coupled to luciferase". The construct is transferred into XTC cells by complexing the DNA with PEI (22 kDA, at 6 equivalents), the transfected cells are cultured in the presence ($10^{-8}$ M) or in the absence (−T3) of T3 thyroid hormone.

Figure 5:
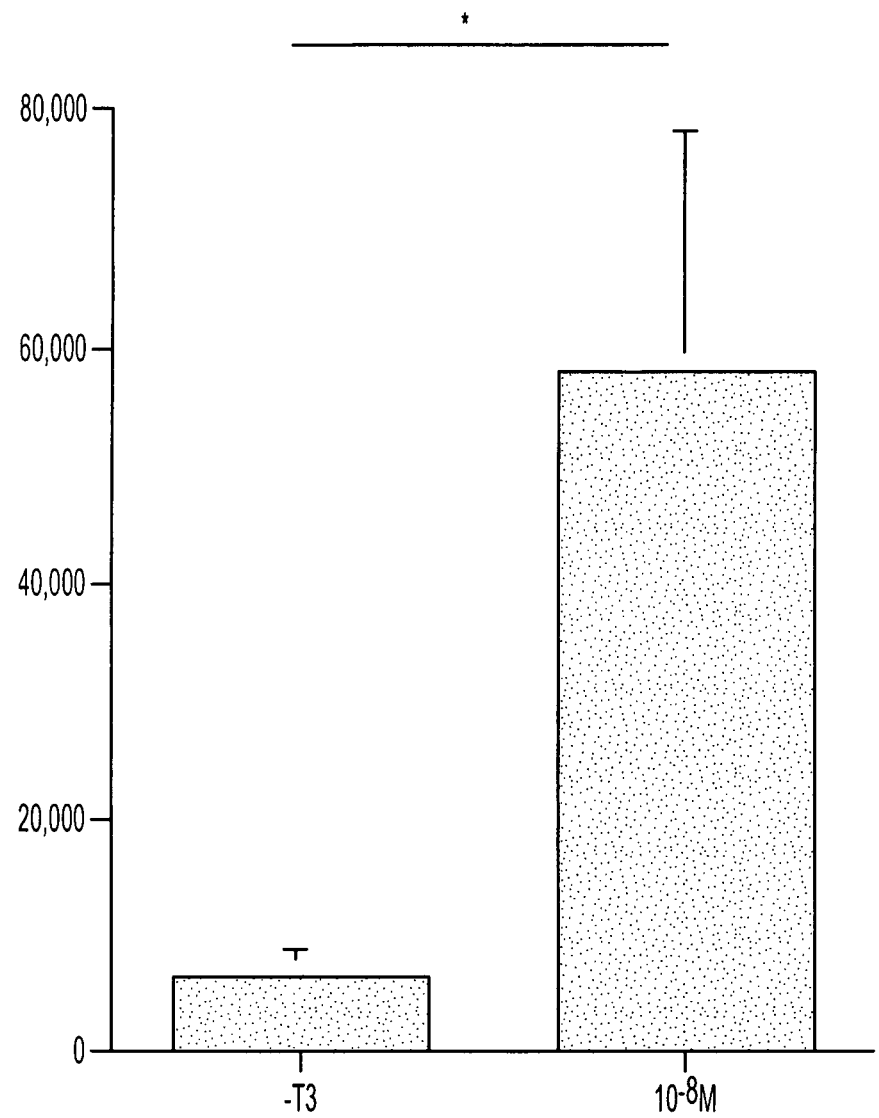

FIG. 5: Somatic transgenesis by injection, into the dorsal muscle of *xenopus*, of the construct TRE-tk-luciferase. The animals are transfected by injection into the dorsal muscle of 1 mg/animal of the construct TRE-tk-luciferase. The animals are then treated in the presence ($10^{-8}$ M) or in the absence (−T3) of T3 thyroid hormone. Four days after treatment, the luciferase expression is measured.

Figure 6:
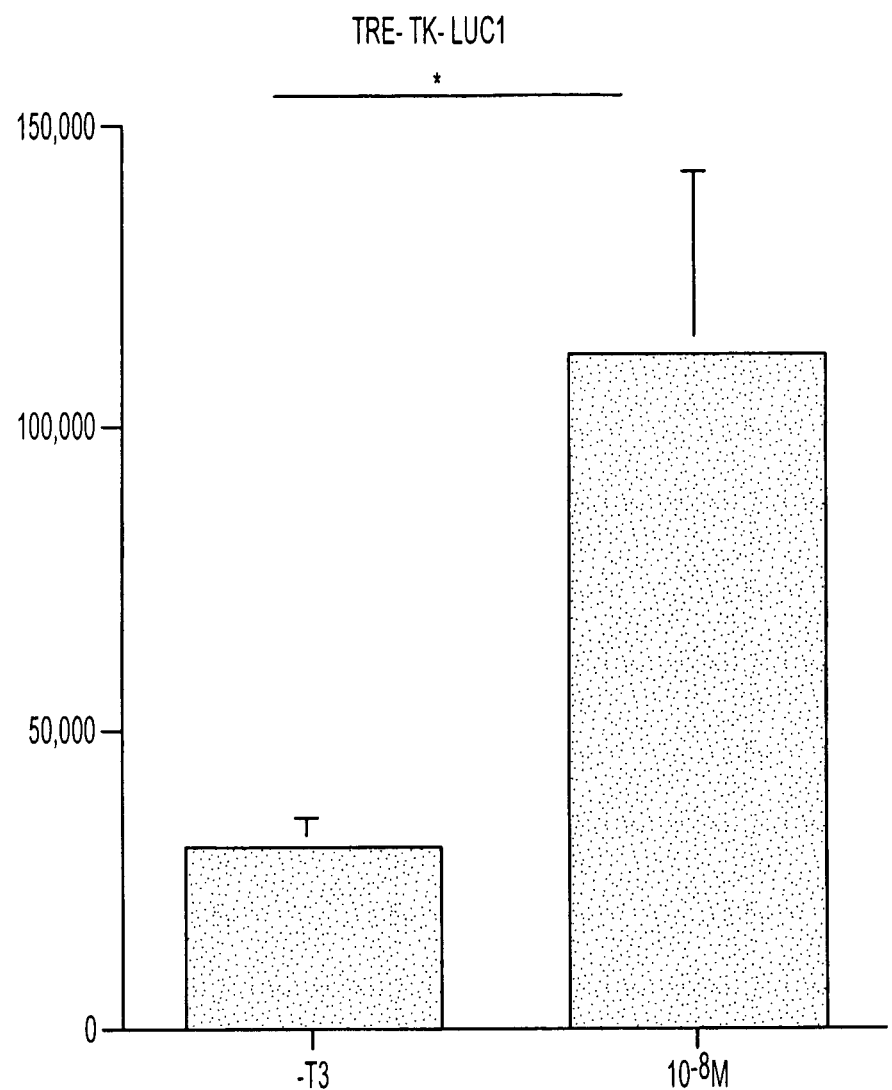

FIG. 6: Somatic transgenesis by injection, into the dorsal muscle of pretreated *xenopus* animals, of the construct TRE-tk-luciferase. The animals are pretreated for 48 hours with $10^{-11}$ M of T3 thyroid hormone, and then rinsed for 24 hours. The animals are then transfected by injection into the dorsal muscle of 1 mg/animal of the construct TRE-tk-luciferase. The animals are then treated for 48 hours ($10^{-8}$ M) or in the absence (−T3) of thyroid hormone. Two days after treatment, the luciferase expression is measured.

Figure 7:
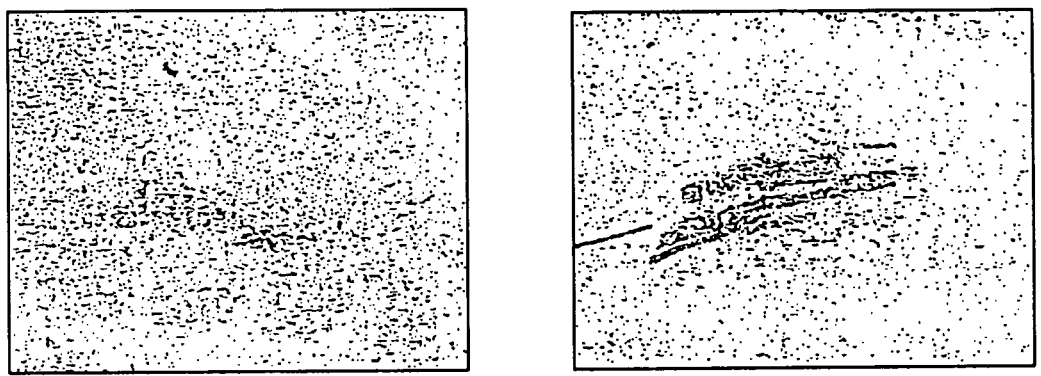

FIG. 7: Somatic transgenesis by injection, into the dorsal muscle of *xenopus*, of the construct TRE-tk-EGFP. The animals are transfected by injection into the dorsal muscle of 1 mg/animal of the construct TRE-tk-EGFP. The animals are then treated for 48 hours in the presence (+T3 10 nM) or in the absence (−T3) of T3 thyroid hormone. The bioluminescence is visible in the cells of the treated animal.

Figure 8:
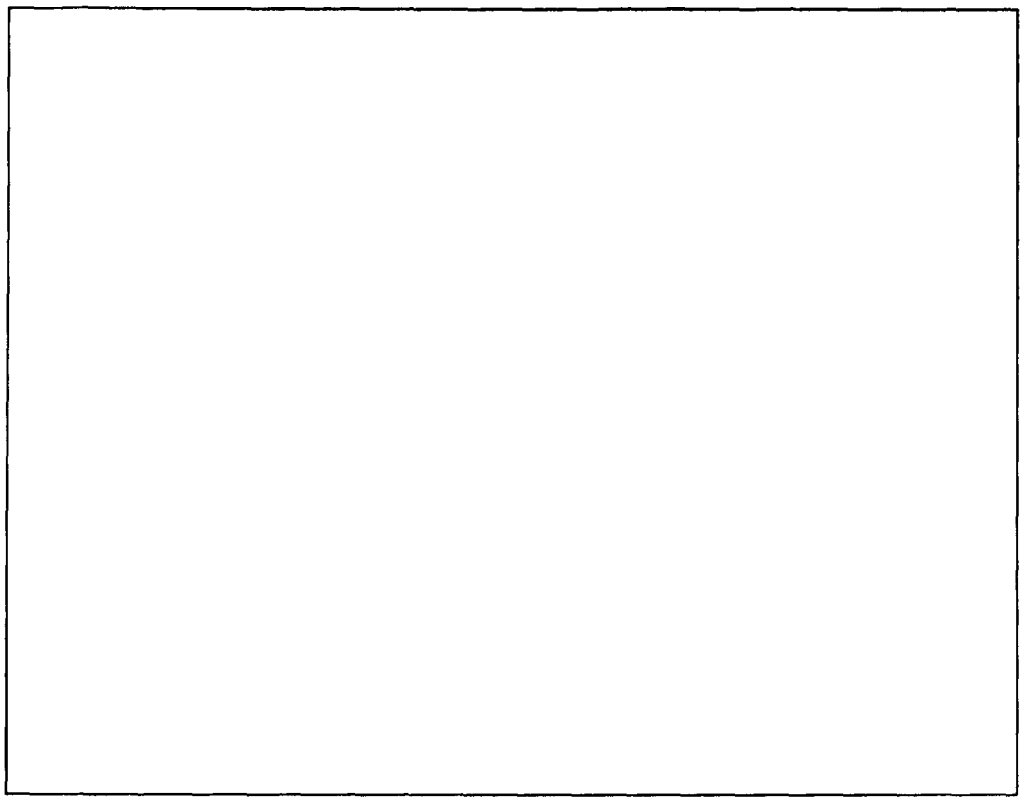

FIG. 8: Ventral view of a tadpole that is transgenic for the construct DR4(X3)-GFP with insulating genetic elements ("insulators"), responding to the presence of thyroid hormone in the water of the aquarium ($10^{-8}$ M) through the emission of fluorescence throughout the nervous system and in the limb buds.

EXAMPLES

1. Materials and Methods 1.1. The Cloning Vector

The expression cassettes are inserted into the basic vector pBluescript II SK (PROMEGA) at the multiple cloning site containing in particular the restriction sites: SacI, SacII, NotI, XbaI, BamHI, SmaI, PstI, EcorI, EcorV, HindIII, SalI, XhoI, ApaI, KpnI.

Preferably, the expression cassette is introduced at the SalI site. The cassette and the vector were linearized beforehand with SalI and the ends were made blunt.

1.2. The Nuclear Hormone Receptor Response Elements

Various TRE (thyroid response element) sequences will be used:
  the rat malic enzyme TRE (Seq ID No. 1),
  one copy of the consensus TRE (DR4) (Seq ID No. 3, No. 5, No. 6, No. 7, No. 9),
  three copies of the consensus TRE (DR4)X3, 4 nucleotides apart.

Various sequences of promoter sequences containing TREs will be used:
  murine myc promoter containing a negative TRE (Perez-Juste et al., 2000) (cloning in the PstI-XhoI sites of pBS-SK II) (Seq ID No. 4),
  promoter of the *xenopus* gene TH/bZIP (Furlow and Brown, 1999) (Seq ID No. 12; accession number AF192492 (gi 6707362) genbank) containing two positive TREs (Seq ID No. 2 and No. 3) (cloning in the SacI-PstI sites of pBS-SK II) (FIG. 1),
  *xenopus* stromelysin 3 promoter containing several TREs (cloning in the HindIII site).

The oligonucleotides containing these sequences are cloned into the vector pBS-SK II (PROMEGA), preferably at the XbaI and BamHI sites.

1.3. The Minimum Promoter

The 170 bp minimum promoter of the herpes simplex virus (HSV) thymidine kinase (TK) gene is isolated by PCR and then cloned into the BamHI-HindIII sites of pBS-SK II, containing the promoter sequences containing the TREs.

The reporter genes are cloned downstream of the TRE-tk sequence.

Next, the "TRE-tk-reporter gene" sequence is excised from the vector pBS-SK II, and its ends are then made blunt in order to be cloned into the vector containing the insulators.

1.4. The Reporter Gene

Initially, the constructs are prepared with the EGFP and firefly luciferase genes.

The following constructs were thus constructed:
TRE (malic enzyme)-TK-EGFP
TRE (malic enzyme)-TK-luciferase
stromelysin-3-luciferase.

Fusion genes will subsequently be generated by combining the sequences encoding the EGFP or RedFep fluorescent proteins (CLONTECH) with the firefly luciferase (PROMEGA) or Renilla luciferase. The EGFP and RedFep cDNA sequences will be amplified by PCR using primers containing KpnI and BglII restriction sites. The amplified fragments will be cloned into these sites in the pGL2 basic vector from PROMEGA, which contains the firefly luciferase gene. The "fluorescent protein/luciferase/polyadenylation signal" sequence block will be extracted from the pGL2 basic vector by digestion with the SmaI and SalI enzymes. The ends will then be made blunt and the digestion fragments will be cloned downstream of the various promoters, in one of the restriction sites of the multiple cloning site of the vector pBS-SK II which is free and located in the position 3' of the promoters, such as for example the SalI site.

The fusion genes will be pretested "empty", i.e. they will be cloned into the BamHI-HindIII site downstream of the HSV TK promoter in pBS-SK II, in order to verify the absence of cryptic nuclear hormone receptor response elements (in particular TREs) capable of influencing the response of the promoters and therefore of behaving like "enhancer" sequences.

1.5. The "Insulator" Sequence

Two insulator sequences are preferably used; that of the chicken beta-globin gene (Seq ID No. 11; accession number AY 040835 (gi:171 49 284) in genbank) and that of the chicken lyzozyme gene (Seq ID No. 10; accession number X98 408 (gi:1403311).

The "insulator" sequences are isolated by polymerase chain reaction (PCR) using chicken genomic DNA or a vector containing it, as DNA matrix. The pair of primers used contains restriction sites in order to facilitate the subsequent cloning. Thus, the "insulator" sequences of the beta-globin gene are cloned into the vector: in the 5' position at the SacI-BamHI sites, in the 3' position at the XhoI-KpnI sites. The "insulator" sequences of the lyzozyme gene are cloned into the vector: in the 5' position at the BamHI-HindIII sites, in the 3' position at the XhoI-KpnI sites.

The "insulator" sequences thus isolated are cloned on either side of the expression cassette containing the reporter gene under the control of a regulatory sequence for transcription selected from the nuclear hormone receptor response elements.

The definitive "promoter-reporter gene" sequences are extracted from PBS-SK II and the ends are made blunt in order to integrate these sequences into the vectors containing the insulators (FIG. 2).

1.6. Somatic Transgenesis

Somatic transgenesis (Ouatas et al., 1998) is used to verify the validity of the constructs (FIG. 3) and their potential regulation by the compounds, such as the T3 thyroid hormone, before use in germinal transgenesis.

The somatic transgenesis is carried out either:
by injection of 1 µl of naked DNA into the dorsal muscle of the embryo. The DNA concentration is 100 ng/µl to 5 µg/µl in 0.07 M NaCL;

by microinjection of 1 µl of DNA/PEI (polyethyleneimine) into the brain of the embryo. The DNA concentration is between 50 and 500 ng/µl in 5% glucose.

The germinal transgenesis is carried out according to the protocol described by Kroll and Amaya (1996).

2. Construct Functionality Assay 2.1. Assays on Cells in Culture

The transgenic constructs are tested in XTC *xenopus* cells in culture.

The XTC cells are obtained from carcasses of *xenopus* tadpoles just before metamorphosis (Pudney et al., 1973). The cells are cultured at ambient temperature, for up to 20 passages.

The cells are transfected by complexing the DNA with 22 kDa polyethyleneimine (PEI) at 6 equivalents (Ouatas et al., 1998).

The protocol makes it possible to rapidly verify the constructs and thus to verify that said constructs respond correctly to the substances, such as the T3 thyroid hormone when it is injected into the cell culture medium.

XTC cells will be produced from transgenic tadpoles in order to perform assays. These transgenic XTC cells may be transfected by means of vectors overexpressing various isoforms of nuclear hormone receptors in order to study the action of endocrine disrupters.

2.2. XTC Cell Transfection with the Stromelysin 3/Luciferase Construct

In the absence of T3 thyroid hormone in the culture medium for the transgenic XTC cells, a basal level of expression of the luciferase reporter protein is observed. The addition of T3 thyroid hormone to the culture medium at a concentration of $10^{-8}$ M induces greater expression of the reporter protein (FIG. 4).

3. Somatic Transgenesis in *Xenopus* with TRE-TK-Luciferase 3.1. The TRE-tk-luciferase construct was injected into the dorsal muscle of a *xenopus* embryo (1 mg/animal). Half the animals are treated with T3 thyroid hormone at $10^{-8}$ M. Four days later, the expression of the reporter gene is measured in the treated ($10^{-8}$ M of T3) and nontreated (−T3) animals. The addition of T3 thyroid hormone to the culture medium at a concentration of $10^{-8}$ M induces much greater expression of the reporter protein (FIG. 5).

3.2. According to an alternative method, the transgenic animals according to the invention are pretreated with perchlorate for one month at 1 g/l, and are then sensitized with the test compound, such as the T3 hormone ($10^{-11}$ M), for 18 to 48 hours without food. The animals are then washed in a medium containing no T3 and are fed for 36 hours. The construct (for example TRE-tk-luciferase) is injected into the dorsal muscle of the *xenopus* embryo (1 mg/animal).

Out of the 24 tadpoles that were pretreated and then subjected to somatic transgenesis, twelve tadpoles are treated for 48 hours with T3 thyroid hormone at $10^{-8}$ M; the other twelve tadpoles that remain serve as a control. The addition of T3 thyroid hormone to the culture medium at a concentration of $10^{-8}$ M induces much greater expression of the reporter protein (FIG. 6).

3.3. The TRE-tk-EGFP construct was injected into the dorsal muscle of a *xenopus* embryo (1 mg/animal). Half the animals are treated with T3 thyroid hormone at 10 nM. Four days later, expression of the reporter gene is detected in the treated (10 nM of T3) and nontreated (−T3) animals. The addition of T3 thyroid hormone to the culture medium at a concentration of 10 nM induces much greater expression of the reporter protein (FIG. 7).

REFERENCES

Arnheiter et al., (1990) Cell 62:51
Argenton et al., (1996) Mol Cell Biol 16:1714-1724
Brinster et al., (1982) Nature 296:39-42
Brown et al., (1987) Cell 49:603-612
Brown et al., (1996) Proc. Natl. Acad. Sci. USA 93: 1924-9
Capecchi et al., (1989) Science 244:1288-1291
Ciana et al. (2001) Mol. Endocrinol 15:1104-13
Coen et al. (2001) Proc. Natl. Acad. Sci. USA 98: 7869-74
Day et al., (1998) Biotechniques 25: 848-50, 852-4, 856
De Luze et al., (1993) Proc. Natl. Acad. Sci. USA 90: 7322-6
Denver et al., (1997) J. Biol. Chem 272: 8179-88
Denver et al., (1999) J. Biol. Chem 274 (33): 23128-34
Deuschle et al., (1990) Science 2: 480-483
Echt et al. (1988) Embo J. 7: 2063-2073
Farsetti et al. (1992) J. Biol. Chem 267: 15784-8
Figge et al., (1988) Cell 49: 603-612
Furlow et al. (1999) Mol. Endocrinol 13: 2076-89
Gossen et al., (1992) Proc. Natl. Acad. Sci. USA 89: 5547-5551)
Hu et al., (1987) Cell 48: 555-556
Hug et al., (1998) Mol. Cell. Biol. 8: 3065
Hynes et al., (1981) Proc. Natl. Acad. Sci. USA 78: 2038-2042
Ishizuya-Oka et al. (1996) Cell Tissue Research Israel et al., (1989) Nucleic Acids Res. 17: 2589-2604
Karsenti et al. (2000) Semin. Cell. Biol 11(5): 343-6
Kitazawa et al. (2002) Biochel Biophys Res Commun 290: 650-655
Klock et al., (1987) Nature 329: 734-736
Kolla et al. (1998) Biophys Res Commun. 266: 5-14
Kroll et al., (1996) Development 122: 3173-83
Kroll and Amaya, (1999) Methods Mol Biol 97: 393-414
Labow et al., (1990) Mol. Cell. Biol. 10: 3343-3356)
Lee et al., (1981) Nature 294: 228-232
Liu et al., (2000) Luminescence 15: 45-9
Luo et al., (2001) Biochem Biophys Res Commun
Mader et al. (1993) Nucleic Acids Res 21: 1125-1132
Mayo et al., (1982) Cell 29: 99-108
Metzger and Feil (1999), Curre. Opion. Biotechnol. 5: 470-476
Namciu et al. (1998) Mol. Cell. Biol 18: 2382-91
Nover et al., (1991) in "Heat Shock Response", e.d.
Nover, L CRC, Boca Raton, Fla. pp. 167-220
Oofusa et al., (2001) Mol. Cell. Endocrinol 181: 97-110
Ouatas et al., (1998) Int. J. Dev. Biol 42: 1159-64
Perez-Juste et al., (2000) J. Biol. Chem 275: 1307-14
Pudney et al. (1973) Experiantia 29: 466-467
Roberto et al., (2000) Endocrinology 141: 4056-4064
Schmidt et al., (1990) Mol. Cell. Biol. 10: 4406-4411
Seark et al., 1985 Mol. Cell. Biol. 5: 1480-1489
Stief et al., (1989) Nature 341: 343-5
Wang et al., (1993) J. Biol. Chem 268 (22): 16270-8
Xiang et al., (1998) Nucleic Acids Research 26: 2034-2035

---

The invention claimed is:

1. A method for identifying the presence of at least one endocrine disrupter environmental pollutant, comprising:
   a) sensitizing with Tri-iodothyronine (T3) hormone a first germinal transgenic *Xenopus* embryo and a second germinal transgenic *Xenopus* embryo;
      wherein said first embryo and said second embryo each comprise in its genome an expression cassette comprising an heterologous promoter operably linked to (i) a regulatory DNA sequence from a vertebrate, said regulatory sequence is a nuclear hormone receptor response element comprising at least SEQ ID NO:2 and SEQ ID NO:3 and is functionally linked upstream of (ii) a DNA element encoding a reporter protein and a polyadenylation signal and (iii) an insulator sequence at each end of the expression cassette;
   b) contacting said first embryo with a first aqueous medium suspected of comprising said at least one environmental pollutant, wherein said first aqueous medium comprises water of a natural aquatic medium;
   c) contacting said second embryo with a second aqueous medium serving as control;
   d) determining expression of the reporter protein in the first embryo and the second embryo; and
   e) comparing the determined expressions to identify the presence or absence of said environmental pollutant in the first aqueous medium.

2. The method of claim 1, wherein said method comprises identifying the presence of two or more endocrine disrupter environmental pollutants, wherein the expression cassette comprises two or more hormone receptor response elements, wherein each response element comprises a distinct reporter protein, and comparing the determined expressions of each reporter protein from control expressions to identify the presence or absence of said two or more environmental pollutants.

3. The method of claim 1, wherein the insulator sequence is from a chicken beta-globin gene or a chicken lyzozyme gene.

4. The method of claim 1, wherein the expression cassette comprises SEQ ID NO: 12.

5. The method of claim 2, wherein a second response element is selected from group consisting of a mineralocorticoid response element (MRE), a glucocorticoid response element (GRE), a progesterone response element (PRE), and an estrogen response element (ERE).

* * * * *